(12) United States Patent  (10) Patent No.: US 6,598,737 B2
Rudnick  (45) Date of Patent: Jul. 29, 2003

(54) ANGLED DISPENSER BOX FOR SUTURES

(75) Inventor: James J. Rudnick, Mahwah, NJ (US)

(73) Assignee: Ethicon, Inc., Somerville, NJ (US)

( * ) Notice: Subject to any disclaimer, the term of this patent is extended or adjusted under 35 U.S.C. 154(b) by 68 days.

(21) Appl. No.: 09/899,624

(22) Filed: Jul. 5, 2001

(65) Prior Publication Data

US 2003/0006149 A1 Jan. 9, 2003

(51) Int. Cl.⁷ ............................................. B65D 83/08
(52) U.S. Cl. ...................... 206/63.3; 206/822; 221/305; 229/108; 229/121; 229/122.1
(58) Field of Search ................... 206/63.3, 123–125, 206/499, 738, 227, 822; 229/108, 122.1, 122.2, 121; 221/92, 124, 131, 191, 194, 281, 303, 305; D6/515, 517

(56) References Cited

U.S. PATENT DOCUMENTS

| | | | | |
|---|---|---|---|---|
| 319,322 A | * | 6/1885 | Roberts | 221/305 |
| 1,007,547 A | * | 10/1911 | Durrum | 221/305 |
| 1,272,965 A | * | 7/1918 | Kartzmark | 221/305 |
| 1,875,781 A | * | 9/1932 | Turner | 229/122.1 |
| 2,980,316 A | * | 4/1961 | Buttery et al. | 229/108 |
| 3,450,308 A | * | 6/1969 | Schoenefeld | 221/305 |
| 4,382,526 A | * | 5/1983 | Stone | 221/305 |
| 4,405,044 A | * | 9/1983 | Flower et al. | 206/438 |
| 5,284,293 A | | 2/1994 | Alpern et al. | |
| 5,447,253 A | | 9/1995 | Williams | |
| 5,860,517 A | | 1/1999 | Gemma, Jr. et al. | |
| 5,957,325 A | * | 9/1999 | Montanez | 221/281 |
| 5,988,367 A | | 11/1999 | Gemma, Jr. et al. | |

* cited by examiner

Primary Examiner—Jim Foster

(57) ABSTRACT

A suture dispenser box is provided that has an angled design such that the suture dispenser box may be received in at least two differently formatted storage racks. The suture dispenser box has a plurality of panels including at least two panels that have approximately a parallelogram shape.

15 Claims, 4 Drawing Sheets

ANGLED DISPENSER BOX FOR SUTURES

FIELD OF THE INVENTION

The present invention relates to a suture dispenser box for suture packages, and more specifically to a suture dispenser box that may be received in differently formatted storage racks.

BACKGROUND OF THE INVENTION

Sutures are typically packaged in individual, sterile packages that contain one or more sutures. The individual packages are stacked in a suture dispenser box, which is configured to sequentially dispense suture packages therefrom. In an operating room setting, a plurality of suture dispenser boxes, which hold various sizes and types of sutures, are held by a common storage rack to facilitate orderly display, selection, and dispensing of the sutures.

Conventionally, suture dispenser boxes are available in two different configurations, each adapted to be received in a corresponding type of storage rack. The first type of suture dispenser box is of the vertically formatted type with a dispensing slot located at the bottom. This arrangement is favored in the North American market, which prefers the vertically formatted suture dispenser box wherein the suture packages are stacked vertically and are withdrawn horizontally from the suture dispenser box.

The second type of suture dispenser box is of the horizontally formatted type. This arrangement is favored in the European market, which prefers the horizontally formatted suture dispenser box wherein the suture packages are stacked horizontally (e.g., index card fashion), and are withdrawn vertically from the suture dispenser box.

Accordingly, there are two conventional types of storage racks, which are configured to receive the above-mentioned suture dispenser boxes. Namely, the North American market employs a vertically formatted storage rack, and the European market employs a horizontally formatted storage rack. FIGS. 1–5 depict prior art suture dispenser boxes and storage racks.

FIGS. 1–2 show a vertically formatted suture dispenser box 10 positioned in a vertically formatted storage rack 12. The width W1 of the vertically formatted suture dispenser box 10 is typically approximately 2.5 inches, the height H1 approximately 5.6 inches, and the length L1 approximately 5.4 inches.

The vertically formatted suture dispenser box 10 has a gravity fed dispensing slot 14 located at a bottom edge 16 thereof that is configured to permit removal of suture packages 17 therefrom. Typically, opposed fingers 18, 18', e.g., a thumb and an index finger, may grasp the suture packages 17 contained in the vertically formatted suture dispenser box 10 at the dispensing slot 14. As shown in FIG. 2, the length L1 of the vertically formatted suture dispenser box 10 exceeds the length X of a support shelf 20 of the vertically formatted storage rack 12, so as to permit access to the dispensing slot 14.

FIGS. 3–4 show a horizontally formatted suture dispenser box 22 positioned in a horizontally formatted storage rack 24. The width W2 of the horizontally formatted suture dispenser box 22 is typically approximately 4.7 inches, the height H2 approximately 2.5 inches, and the length L2 approximately 5.6 inches. Note that the dimensions of the horizontally formatted suture dispenser box 22 approximate those of a single compartment 26 in the horizontally formatted storage rack 24.

Thus, the dimensions of the vertically formatted suture dispenser box 10 are approximately 2.5×5.6×5.4 inches. If the horizontally formatted suture dispenser box 22 is reoriented such that its dimensions most closely approximate the foregoing dimensions of the vertically formatted suture dispenser box 10, the dimensions of the horizontally formatted suture dispenser box 22 can be noted to be approximately 2.5×5.6×4.7 inches.

Because the suture dispenser boxes 10, 22 described above have different dimensions, the suture dispenser boxes 10, 22 are not compatible for use in both types of racks 12, 24. That is, the physical dimensions of the vertically formatted suture dispenser box 10 (FIGS. 1–2) will not fit into the horizontally formatted storage rack 24 (FIGS. 3–4) because it is larger.

The alternative approach of inserting the smaller, horizontally formatted suture dispenser box 22 in the vertically formatted storage rack 12 also has drawbacks. For example, prior attempts to use a horizontally formatted suture dispenser box 22 in a vertically formatted storage rack 12 have included adding a dispensing slot (like the slot 16 of FIG. 1) to the horizontally formatted suture dispenser box 22 and placing the horizontally formatted suture dispenser box 22 in the vertically formatted storage rack 12. Although the physical dimensions of the horizontally formatted suture dispenser box 22 (FIGS. 3–4) allow it to fit into the vertically formatted storage rack 12, FIG. 5 illustrates one problem associated with this approach.

FIG. 5 shows the horizontally formatted suture dispenser box 22 reoriented and positioned in the vertically formatted storage rack 12. Because the width W2 of the horizontally formatted suture dispenser box 22 is less than length X of the support shelf 20 of the vertically formatted storage rack 12, the support shelf 20 blocks access to a dispensing slot 27 that may be formed in an edge 28 of the horizontally formatted suture dispenser box 22.

U.S. Pat. No. 5,988,367 discloses a horizontally formatted suture dispenser box, which is placed in a sleeve with a spacer. When used in a vertically formatted storage rack, the spacer causes the horizontally formatted suture dispenser box to extend beyond the support shelf of a vertically formatted storage rack 12 to facilitate access to a dispenser slot. When used in a horizontally formatted storage rack, the sleeve and spacer assembly are discarded, generating waste.

The construction of two types of suture dispenser boxes results in increased manufacturing, distribution, and stocking costs. Accordingly, there is a need for a single novel suture dispenser box that may be compatible with at least the two differently formatted storage racks described above, and that may overcome the disadvantages of the prior art.

SUMMARY OF THE INVENTION

A suture dispenser box is disclosed which has a hollow therein for receiving a plurality of suture packages, and which has a generally prismatic shape. A plurality of panels cooperate so as to form the suture dispenser box. The panels are sized and shaped such that at least two panels have at least two edges intersecting at an acute angle.

Other features and aspects of the present invention will become more fully apparent from the following detailed description of the exemplary embodiment, the appended claims and the accompanying drawings.

BRIEF DESCRIPTION OF THE DRAWINGS

For a more complete understanding of the present invention, reference is made to the following detailed description of the exemplary embodiment considered in conjunction with the accompanying drawings, in which.

DETAILED DESCRIPTION OF THE EXEMPLARY EMBODIMENT

A suture dispenser box is disclosed that is compatible with at least two differently formatted storage racks (e.g., a conventional, horizontally formatted storage rack, a conventional, vertically formatted storage rack, etc.). The suture dispenser box may be made from paper board materials, which are suitable for automation.

Figure 1:
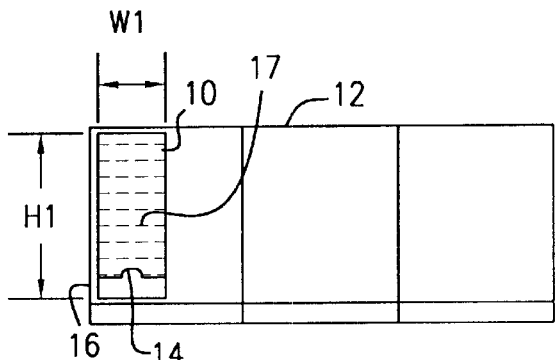
FIGS. 1–2 are schematic front and side views, respectively, of a vertically formatted suture dispenser box positioned in a vertically formatted storage rack as known in the prior art.
Figure 2:
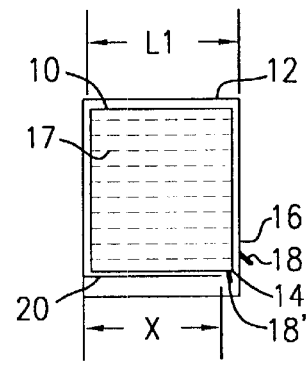
Figure 3:
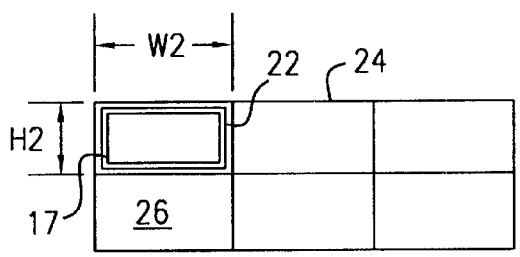
FIGS. 3–4 are a front and top view, respectively, of a horizontally formatted suture dispenser box positioned in a horizontally formatted storage rack as known in the prior art.
Figure 4:
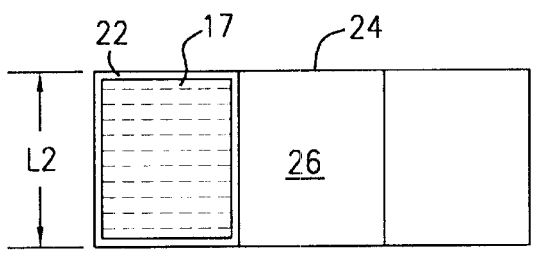
Figure 5:
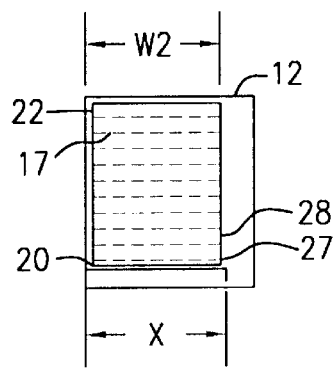
FIG. 5 is a side view of the horizontally formatted suture dispenser box of FIGS. 3–4 reoriented and positioned in the vertically formatted storage rack of FIGS. 1–2 in a manner known in the prior art.
Figure 6:
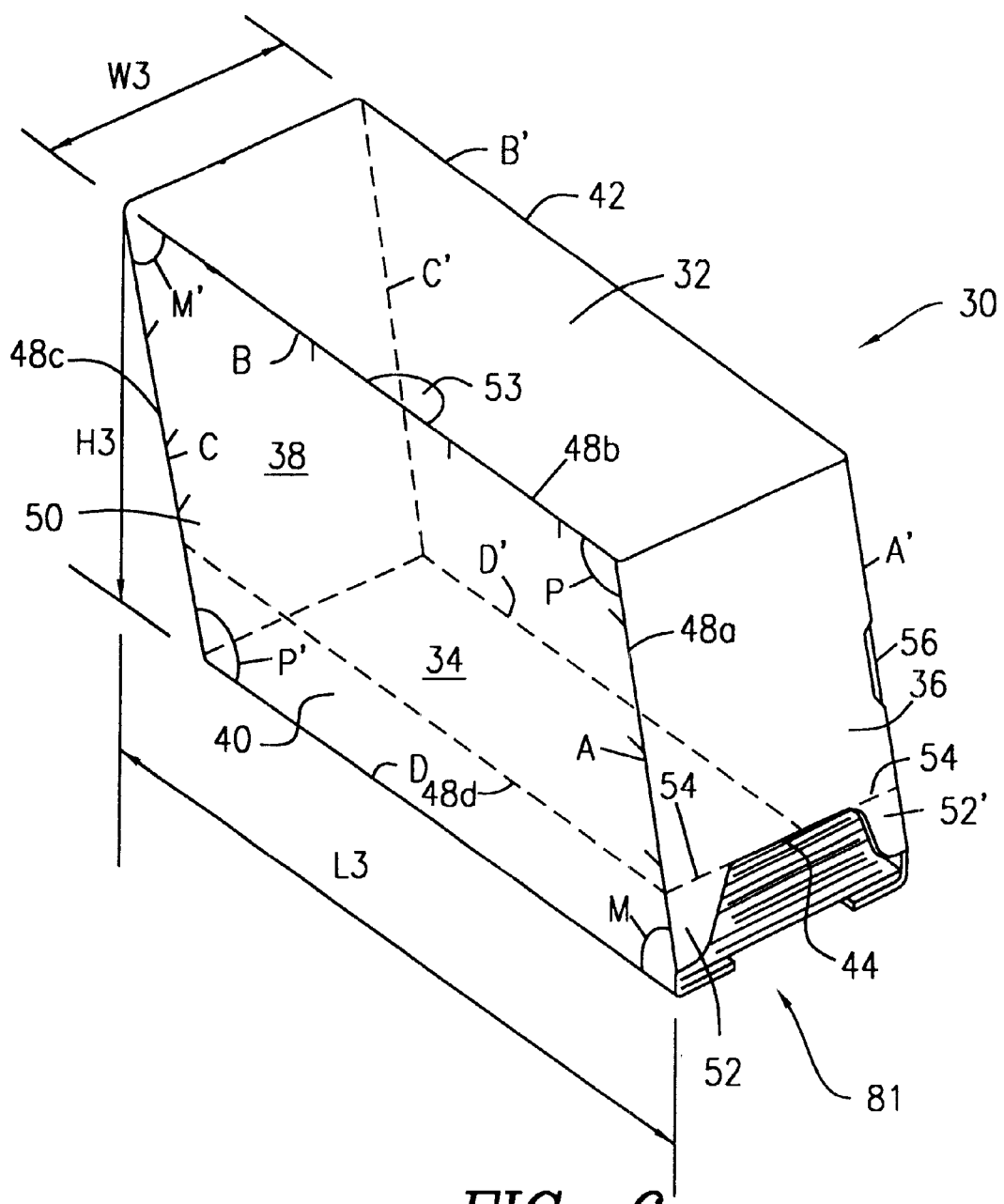
FIG. 6 is a front perspective view of a suture dispenser box in accordance with an exemplary embodiment of the present invention.

FIG. 6 shows a suture dispenser box 30 in accordance with the present invention. The suture dispenser box 30 has top, bottom, front, back, and opposing side panels 32, 34, 36, 38, 40, 42, respectively. The front panel 36 has a slot 44, which is disposed proximate a convergence of the front panel 36 and the bottom panel 34. The slot 44 is configured to permit horizontal removal of the suture packages 17 (see FIG. 8) from the suture dispenser box 30 when it is vertically oriented.

The side panel 40 has perforation lines 48a–d, which define the boundaries of a sub-panel 50 of the side panel 40. The sub-panel 50 can be completely removed by tearing the perforation lines 48a–d to expose an access opening 51 (see FIG. 9). Alternatively, the perforation line 48d can be a creased line adapted to function like a living hinge, whereby the sub-panel 50 can, after tearing the perforation lines 48a–c, pivot about the creased line to expose the access opening 51. Regardless of whether the sub-panel 50 is hinged or is removable, the resulting access opening 51 permits vertical removal of the suture packages 17 from the suture dispenser box 30 when it is horizontally oriented.

The top panel 32 has a finger access cutout 53 removably covered by an extension of the sub-panel 50. The finger access cutout 53 provides increased access to the suture packages 17, so as to facilitate removal of the suture packages 17 from the suture dispenser box 30 when it is horizontally oriented.

The front panel 36 has a pair of deflectable tongues 52, 52' positioned adjacent the slot 44. The deflectable tongues 52, 52' are attached to the main portion of the front panel 36 at a score or fold line 54.

Each side panel 40, 42 has four peripheral edges, which form a parallelogram shape, e.g., the side panel 40 has edges A, B, C, D and the side panel 42 has edges A', B', C', D'. An opening 56 disposed on the peripheral edge A' of the suture dispenser box 30 permits viewing the suture packages 17 in the suture dispenser box 30 to ascertain the quantity of suture packages 17 remaining therein.

Note that adjacent peripheral edges A,D and B,C of the side panel 40 intersect at acute angles M, M', respectively, while adjacent peripheral edges A,B and D,C intersect at obtuse angles P, P', respectively. The side panel 42 has a similar configuration. In an exemplary embodiment, the acute angles M, M' may be selected to have a value of approximately 85 degrees, and the obtuse angles P, P' may be selected to have a value of approximately 95 degrees. It should be noted that the angles shown in FIG. 6 have been exaggerated to illustrate an angled design.

It will be understood that acute angles M, M' and obtuse angles P, P' may have other values and that the angles M, M' and/or the angles P, P' do not have to be equal. Likewise, the shape of the side panels 40, 42 need not be identical.

As shown in FIG. 6, the effective dimensions of the suture dispenser box 30 may be selected to exhibit an approximate width W3 of 2.30 inches, an effective height (altitude) H3 of approximately 5.59 inches, and an effective length (plan projection) L3 of approximately 4.99 inches.

Thus, the suture dispenser box 30 has a generally prismatic shape with effective dimensions of approximately 2.30×5.59×4.99 inches when the suture dispenser box 30 is vertically oriented. It will be understood that the above dimensions for the suture dispenser box 30 are merely exemplary and that the suture dispenser box 30 may have other dimensions.

Figure 7:
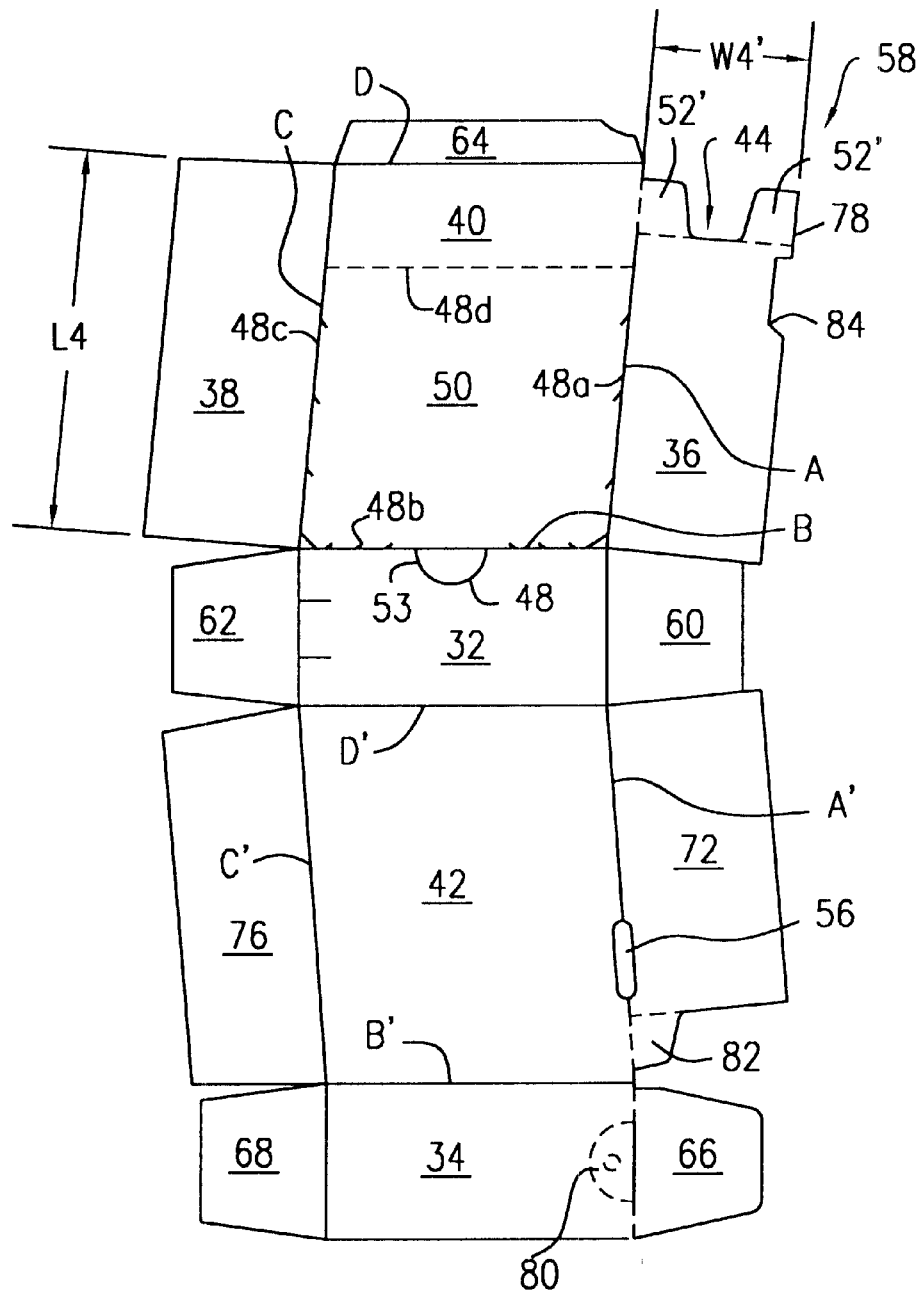
FIG. 7 is a plan view of a blank used to produce the suture dispenser box of FIG. 6.

FIG. 7 shows a blank 58 used to produce the suture dispenser box 30. The blank 58 includes the top, bottom, front, back, and side panels 32, 34, 36, 38, 40, 42, respectively. The top panel 32 has the perforation line 48, which defines the finger access slot 53 and which extends around the periphery of the sub-panel 50.

A pair of tabs 60, 62 is attached adjacent the top panel 32. The tabs 60, 62 underlie the front panel 36 (and/or a support panel 72 which underlies the front panel 36), and the back panel 38 (and/or a support panel 76 which underlies the back panel 38), respectively, when the blank 58 is folded. Glue may be applied to the tabs 60, 62 and the support panels 72, 76 to provide stability to the suture dispenser box 30. The bottom panel 34 extends from the side panel 42 and a foldable tab 64 extends from the side panel 40, which is glued or otherwise adhered to the bottom panel 34 in a conventional manner to form the suture dispenser box 30. The bottom panel 34 has two support tabs 66, 68 to provide further stability to the suture dispenser box 30 and also may be adhesively attached to the front and back panels 36, 38 and/or the support panels 72, 76, respectively.

The slot 44 is positioned adjacent a finger access cutout 80 in the bottom panel 34 when the suture dispenser box 30 is assembled. Removal of the finger access cutout 80 also causes the support tab 66 or a portion thereof to be torn from the bottom panel 34. The slot 44 and the finger access cutout 80 form a gravity fed dispensing slot 81 (FIG. 6), which is configured to permit horizontal removal of the suture packages 17 (FIG. 6) in the suture dispenser box 30 when it is vertically oriented.

The deflectable tongues 52, 52' are positioned adjacent the slot 44, with the deflectable tongue 52' overlapping an optional deflectable tongue 82, when the blank 58 is folded. The cutout 84 in the front panel 36 aligns with the opening 56 when the blank 58 is folded to form the suture dispenser box 30.

As shown in FIG. 7, the extent or length of sides A, C, A', C' may be selected to be approximately 5.61 inches, the extent or length of sides B, D, B', D' may be selected to be approximately 4.50 inches, and the width W4' of the front panel 36 may be selected to be approximately 2.30 inches.

Figure 8:
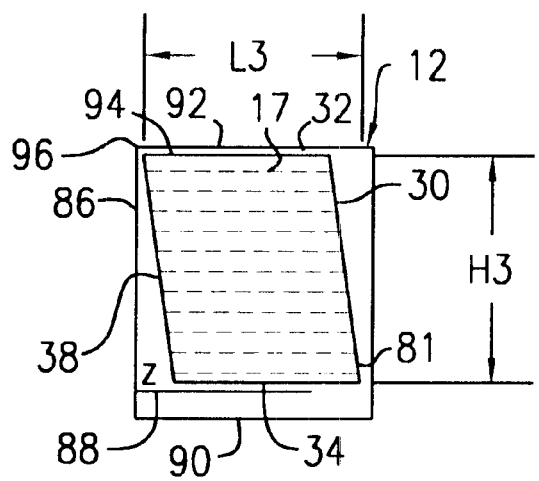
FIG. 8 is a schematic side view of the suture dispenser box of FIGS. 6–7 positioned in a vertically formatted storage rack.

FIG. 8 shows the suture dispenser box 30 of the present invention positioned in a conventional vertically formatted storage rack 12. The vertically formatted storage rack 12 has a rear wall 86, a support shelf 88, a bottom wall 90, and a top wall 92. A retention catch 94, shown schematically in FIG. 8, extends down from the vertically formatted storage rack 12 proximate a corner 96 formed by the rear wall 86 and the top wall 92. The retention catch 94 prevents inadvertent withdrawal of the suture dispenser box 30 when suture packages 17 are withdrawn therefrom. The retention catch 94 may comprise any mechanism (e.g., a resilient member) configured to bias the suture dispenser box 30 toward the rear wall 86 or toward the support shelf 88 of the vertically formatted storage rack 12.

As shown in FIG. 8, the back panel 38 of the suture dispenser box 30 is positioned adjacent the rear wall 86 of the vertically formatted storage rack 12, and the bottom panel 34 is positioned adjacent the support shelf 88. Unlike the prior art, the back panel 38 of the suture dispenser box 30 intersects the support shelf 88 of the vertically formatted storage rack 12 at an acute angle Z, and the back panel 38 and the rear wall 86 are not parallel.

The angled design of the suture dispenser box 30 positions the dispensing slot 81 beyond the support shelf 88 to enable suture packages 17 to be grasped and withdrawn from the suture dispenser box 30. The angled suture dispenser box 30 also simultaneously causes the retention catch 94 to engage the top panel 32 proximate the back panel 38. The angled back panel 38 directs the suture packages 17 forwardly toward the dispensing slot 81 as successive suture packages 17 are dispensed.

Figure 9:
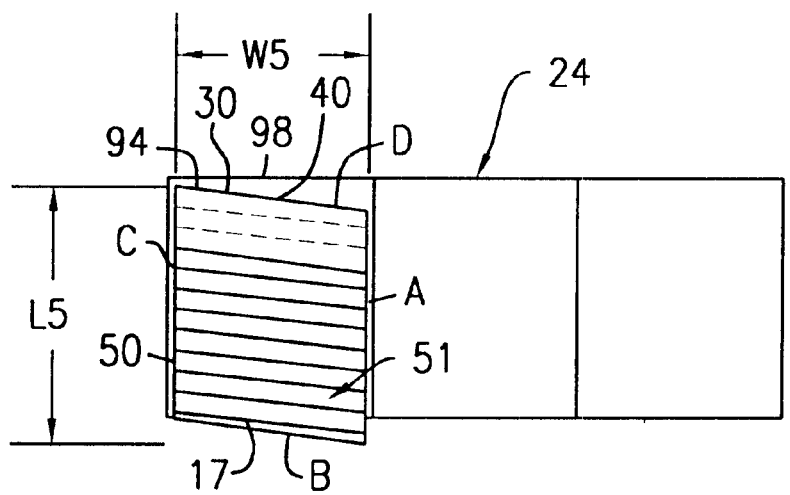
FIG. 9 is a schematic plan view of the suture dispenser box of FIGS. 6–8 positioned in a horizontally formatted storage rack.

FIG. 9 shows the suture dispenser box 30 of the present invention positioned in a conventional horizontally formatted storage rack 24. The suture dispenser box 30 is positioned in the horizontal orientation. The effective width W5 of the suture dispenser box 30 may be selected to be approximately 4.48 inches, the effective height is the same as W4 shown in FIG. 7 or approximately 2.30 inches, and the effective length L5 approximately 6.00 inches. Thus, the suture dispenser box 30 has dimensions of approximately 4.48×2.30×6.00 inches when it is horizontally oriented.

Exposing the access opening 51, whether by pivoting the sub-panel 50 away from the side panel 40 or by entirely removing it from the sub-panel 40, permits vertical withdrawal of the suture packages 17 from the suture dispenser box 30. As shown in FIG. 9, the peripheral edge B and the peripheral edge D of the side panel 40 are not parallel to a rear wall 98 of the horizontally formatted storage rack 24, but this has no effect on dispensing functionality. Note that the effective length L5 of the suture dispenser box 30 exceeds the length of a single compartment 26 in the horizontally formatted storage rack 24, but this also has no effect on dispensing functionality.

As is evident from the description above, the suture dispenser box 30 may be compatible with conventional vertically and horizontally formatted storage racks 12, 24 without the use of spacers or sleeves. Because no spacers or sleeves are used, the storage racks 12, 24 are more efficiently filled when the suture dispenser box 30 is employed, i.e., no space is wasted by the use of spacers.

The foregoing description discloses only the preferred embodiments of the invention. Modifications of the above-disclosed apparatus that fall within the scope of the invention will be readily apparent to those of ordinary skill in the art. While the present invention has been disclosed in connection with the preferred embodiment thereof, it should be understood that other embodiments may fall within the spirit and scope of the invention, as defined by the following claims.

The invention claimed is:

1. A suture dispenser box comprising:
a plurality of panels cooperating so as to form said suture dispenser box having a hollow therein for receiving a plurality of suture packages and having a generally prismatic shape, said plurality of panels including a top panel, a front panel, a bottom panel, a back panel and a pair of side panels, said top panel, said front panel, said bottom panel, said back panel and said pair of side panels being positioned relative to one another so as to form said hollow, each of said pair of side panels having at least one pair of first edges, which intersect at an obtuse angle, and at least one pair of second edges, which intersect at an acute angle, each of said pair of side panels having approximately a parallelogram shape, said front panel having a slot disposed proximate an intersection of said front panel and said bottom panel, said slot configured so as to permit horizontal removal of suture packages contained in said hollow when said suture dispenser box is vertically oriented, one of said pair of side panels having an access opening covered by a sub-panel, and said access opening permitting vertical removal of suture packages contained in said hollow when said suture dispenser box is horizontally oriented.

2. The suture dispenser box of claim 1, wherein said access opening is adjacent said top panel, and said top panel has a finger access cutout removably covered by an extension of said sub-panel, said finger access cutout providing increased access to suture packages contained in said hollow so as to facilitate removal of suture packages therefrom.

3. The suture dispenser box of claim 1, wherein said sub-panel is removable.

4. The suture dispenser box of claim 1, wherein said sub-panel forms a hinged cover over said access opening.

5. The suture dispenser box of claim 1, wherein said front panel has an opening therein configured so as to permit viewing of suture packages contained in said hollow.

6. The suture dispenser box of claim 1, wherein one of said at least one pair of first edges is positioned adjacent said front panel, another of said at least one pair of first edges being positioned adjacent said top panel and intersecting said one of said at least one pair of first edges at a first obtuse angle, one of said at least one pair of second edges being positioned adjacent said back panel and intersecting said another of said at least one pair of first edges at a first acute angle, and another of said at least one pair of second edges being positioned adjacent said bottom panel, intersecting said one of said at least one pair of second edges at a second obtuse angle and intersecting said one of said at least one pair of first edges at a second acute angle.

7. The suture dispenser box of claim 6, wherein said at least one pair of first edges and said at least one pair of second edges are positioned relative to one another such that said first and second acute angles are diagonally opposed and said first and second obtuse angles are diagonally opposed.

8. The suture dispenser box of claim 6, wherein at least one of said first and second acute angles has a value of approximately 85 degrees and further wherein at least one of said first and second obtuse angles has a value of approximately 95 degrees.

9. A suture dispenser box comprising:

a plurality of panels cooperating so as to form said suture dispenser box having a hollow therein for receiving a plurality of suture packages and having a generally prismatic shape, said plurality of panels including a top panel, a front panel, a bottom panel, a back panel and a pair of side panels, said top panel, said front panel, said bottom panel, said back panel and said pair of side panels being positioned relative to one another so as to form said hollow, each of said pair of side panels having at least one pair of first edges, which intersect at an obtuse angle, and at least one pair of second edges, which intersect at an acute angle, each of said pair of side panels having approximately a parallelogram shape, one of said pair of side panels having an access opening covered by a sub-panel, said access opening permitting vertical removal of suture packages contained in said hollow when said suture dispenser box is horizontally oriented, said access opening being positioned adjacent said top panel, said top panel having a finger access cutout removably covered by an extension of said sub-panel, and said finger access cutout providing increased access to suture packages contained in said hollow so as to facilitate removal of suture packages therefrom.

10. The suture dispenser box of claim 9, wherein said front panel has an opening therein configured to permit viewing of suture packages contained in said hollow.

11. The suture dispenser box of claim 9, wherein one of said at least one pair of first edges is positioned adjacent said front panel, another of said at least one pair of first edges being positioned adjacent said top panel and intersecting said one of said at least one pair of first edges at a first obtuse angle, one of said at least one pair of second edges being positioned adjacent said back panel and intersecting said another of said at least one pair of first edges at a first acute angle, and another of said at least one pair of second edges being positioned adjacent said bottom panel, intersecting said one of said at least one pair of second edges at a second obtuse angle and intersecting said one of said at least one pair of first edges at a second acute angle.

12. The suture dispenser box of claim 11, wherein said front panel has a slot disposed proximate said second acute angle, said slot being configured to permit horizontal removal of suture packages contained in said hollow when said suture dispenser box is vertically oriented.

13. The suture dispenser box of claim 12, wherein said suture dispenser box is configured to direct suture packages contained in said hollow forwardly toward said slot when said suture dispenser box is vertically oriented.

14. The suture dispenser box of claim 11, wherein said at least one pair of first edges and said at least one pair of second edges are positioned relative to one another such that said first and second acute angles are diagonally opposed and said first and second obtuse angles are diagonally opposed.

15. The suture dispenser box of claim 11, wherein at least one of said first and second acute angles has a value of approximately 85 degrees and further wherein at least one of said first and second obtuse angles has a value of approximately 95 degrees.

* * * * *